(12) United States Patent
Brooks et al.

(10) Patent No.: US 12,311,070 B2
(45) Date of Patent: May 27, 2025

(54) ROBOTIC SOCIAL INTERACTION

(71) Applicant: Robust AI, Inc., Palo Alto, CA (US)

(72) Inventors: Rodney Allen Brooks, San Francisco, CA (US); Dylan Bourgeois, San Francisco, CA (US); Crystal Chao, San Francisco, CA (US); Alexander Jay Bruen Trevor, San Francisco, CA (US); Mohamed Rabie Amer, San Francisco, CA (US); Anthony Sean Jules, Hillsborough, CA (US); Gary Fred Marcus, Vancouver (CA); Michelle Ho, San Francisco, CA (US)

(73) Assignee: Robust AI, Inc., San Carlos, CA (US)

( * ) Notice: Subject to any disclaimer, the term of this patent is extended or adjusted under 35 U.S.C. 154(b) by 1019 days.

(21) Appl. No.: 17/207,207

(22) Filed: Mar. 19, 2021

(65) Prior Publication Data
US 2021/0346557 A1 Nov. 11, 2021

Related U.S. Application Data

(60) Provisional application No. 63/022,349, filed on May 8, 2020, provisional application No. 63/022,348, filed on May 8, 2020.

(51) Int. Cl.
G01C 21/00 (2006.01)
A47L 11/40 (2006.01)
(Continued)

(52) U.S. Cl.
CPC .............. A61L 2/24 (2013.01); A47L 11/4011 (2013.01); A47L 11/405 (2013.01); A61L 2/10 (2013.01);
(Continued)

(58) Field of Classification Search
CPC .......... A61L 2/24; A61L 2/10; A61L 2202/11; A61L 2202/14; A61L 2202/16;
(Continued)

(56) References Cited

U.S. PATENT DOCUMENTS 4,028,135 A 6/1977 Vig et al.
6,865,446 B2 3/2005 Yokono et al.
(Continued)

FOREIGN PATENT DOCUMENTS

JP 2021175631 11/2021
WO 2018233858 A1 12/2018

OTHER PUBLICATIONS

Int'l Application Serial No. PCT/US21/24416, Int'l Search Report and Written Opinion mailed Jun. 10, 2021.
(Continued)

Primary Examiner — Ian Jen
(74) Attorney, Agent, or Firm — Polygon IP, LLP

(57) ABSTRACT

A robot may identify a human located proximate to the robot in a physical environment based on sensor data captured from one or more sensors on the robot. A trajectory of the human through space may be predicted. When the predicted trajectory of the human intersects with a current path of the robot, an updated path to a destination location in the environment may be determined so as to avoid a collision between the robot and the human along the predicted trajectory. The robot may then move along the determined path.

12 Claims, 16 Drawing Sheets
(3 of 16 Drawing Sheet(s) Filed in Color)

(51) Int. Cl.

| | | |
|---|---|---|
| A61L 2/10 | (2006.01) | |
| A61L 2/24 | (2006.01) | |
| B25J 9/16 | (2006.01) | |
| B25J 11/00 | (2006.01) | |
| B25J 15/00 | (2006.01) | |
| B25J 18/00 | (2006.01) | |
| G01C 21/20 | (2006.01) | |
| G02B 3/08 | (2006.01) | |
| G02B 5/20 | (2006.01) | |
| G02B 5/26 | (2006.01) | |
| G02B 26/08 | (2006.01) | |
| G05D 1/00 | (2006.01) | |
| G05D 1/249 | (2024.01) | |
| G05D 1/617 | (2024.01) | |
| G05D 1/689 | (2024.01) | |

(52) U.S. Cl.
CPC ........... *B25J 9/1664* (2013.01); *B25J 9/1674* (2013.01); *B25J 11/0085* (2013.01); *B25J 15/0014* (2013.01); *B25J 18/00* (2013.01); *G01C 21/206* (2013.01); *G02B 3/08* (2013.01); *G02B 5/208* (2013.01); *G02B 5/26* (2013.01); *G02B 26/0875* (2013.01); *G05D 1/0094* (2013.01); *G05D 1/0214* (2013.01); *G05D 1/0246* (2013.01); *G05D 1/249* (2024.01); *G05D 1/617* (2024.01); *G05D 1/689* (2024.01); *A47L 2201/04* (2013.01); *A61L 2202/11* (2013.01); *A61L 2202/14* (2013.01); *A61L 2202/16* (2013.01); *A61L 2202/17* (2013.01); *A61L 2202/25* (2013.01); *G05B 2219/50391* (2013.01)

(58) Field of Classification Search
CPC ............. A61L 2202/17; A61L 2202/25; A47L 11/4011; A47L 11/405; A47L 2201/04; A47L 9/2857; B25J 9/1664; B25J 9/1674; B25J 11/0085; B25J 15/0014; B25J 18/00; G01C 21/206; G02B 3/08; G02B 5/208; G02B 5/26; G02B 26/0875; G05D 1/0094; G05D 1/0214; G05D 1/0246; G05D 1/249; G05D 1/617; G05D 1/689; G05D 1/0248; G05D 1/0274; G05B 2219/50391; G05B 15/02; G05B 2219/40411

See application file for complete search history.

(56) References Cited

U.S. PATENT DOCUMENTS

| | | | |
|---|---|---|---|
| 6,925,679 B2 | 8/2005 | Wallach et al. | |
| 8,428,781 B2 | 4/2013 | Chang et al. | |
| 8,706,298 B2* | 4/2014 | Goulding | G06N 3/008 |
| | | | 700/251 |
| 8,909,370 B2 | 12/2014 | Stiehl et al. | |
| 9,079,307 B2* | 7/2015 | Fernando | B25J 9/1676 |
| 9,588,519 B2* | 3/2017 | Stubbs | G05D 1/0261 |
| 9,649,766 B2* | 5/2017 | Stubbs | G05D 1/0261 |
| 9,757,486 B2 | 9/2017 | Dobrinsky et al. | |
| 10,279,476 B2 | 5/2019 | Jaekel et al. | |
| 10,435,279 B2* | 10/2019 | Taylor | B60L 53/63 |
| 10,478,973 B2* | 11/2019 | Deyle | G08B 13/196 |
| 10,705,528 B2* | 7/2020 | Wierzynski | G05D 1/0061 |
| 10,733,445 B1* | 8/2020 | Coe | G06V 20/10 |
| 10,793,291 B2 | 10/2020 | Brown et al. | |
| 10,919,555 B1 | 2/2021 | Spruill | |
| 11,099,562 B1 | 8/2021 | Ebrahimi Afrouzi | |
| 11,345,032 B2* | 5/2022 | Taira | B25J 5/007 |
| 11,409,295 B1* | 8/2022 | Samdaria | G05D 1/0217 |
| 11,498,587 B1* | 11/2022 | Mitlin | G05D 1/0214 |
| 11,548,159 B1 | 1/2023 | Ebrahimi Afrouzi | |
| 2008/0009967 A1* | 1/2008 | Bruemmer | G05D 1/0088 |
| | | | 700/245 |
| 2008/0106374 A1 | 5/2008 | Sharbaugh | |
| 2008/0197226 A1 | 8/2008 | Cooper | |
| 2009/0234499 A1* | 9/2009 | Nielsen | B25J 9/161 |
| | | | 700/250 |
| 2010/0222925 A1* | 9/2010 | Anezaki | G05D 1/0221 |
| | | | 700/253 |
| 2010/0234993 A1 | 9/2010 | Seelinger | |
| 2012/0305787 A1 | 12/2012 | Henson | |
| 2015/0088310 A1 | 3/2015 | Pinter | |
| 2016/0271803 A1 | 9/2016 | Stewart | |
| 2016/0317690 A1 | 11/2016 | Dayton | |
| 2016/0354931 A1 | 12/2016 | Jones et al. | |
| 2017/0049915 A1 | 2/2017 | Brais | |
| 2017/0080117 A1 | 3/2017 | Gordon | |
| 2017/0097232 A1 | 4/2017 | Anderson-Sprecher | |
| 2017/0190051 A1* | 7/2017 | O'Sullivan | G05D 1/0088 |
| 2017/0225334 A1* | 8/2017 | Deyle | B25J 5/007 |
| 2017/0225336 A1* | 8/2017 | Deyle | B25J 11/008 |
| 2017/0246331 A1 | 8/2017 | Lloyd | |
| 2017/0285635 A1* | 10/2017 | Sisbot | G06Q 10/06311 |
| 2018/0001946 A1 | 1/2018 | Yokoya | |
| 2018/0101179 A1 | 4/2018 | Louey | |
| 2018/0104368 A1 | 4/2018 | Dobrinsky et al. | |
| 2018/0116479 A1 | 5/2018 | Gilbert, Jr. et al. | |
| 2018/0161986 A1 | 6/2018 | Kee | |
| 2018/0354539 A1 | 12/2018 | Casey | |
| 2019/0009412 A1* | 1/2019 | Khan | B25J 9/1697 |
| 2019/0217477 A1 | 7/2019 | Paepcke | |
| 2019/0219409 A1 | 7/2019 | Tan et al. | |
| 2019/0224853 A1 | 7/2019 | Gewecke et al. | |
| 2020/0086487 A1 | 3/2020 | Johnson et al. | |
| 2020/0094418 A1 | 3/2020 | Mika et al. | |
| 2020/0189120 A1 | 6/2020 | Weaver | |
| 2020/0401133 A1 | 12/2020 | Armbrust | |
| 2021/0053207 A1 | 2/2021 | Romanov et al. | |
| 2021/0138912 A1 | 5/2021 | Yamasaki | |
| 2021/0155464 A1 | 5/2021 | Takai | |
| 2021/0178001 A1 | 6/2021 | Bonutti | |
| 2021/0191405 A1* | 6/2021 | Ma'as | G06N 3/044 |
| 2021/0259497 A1 | 8/2021 | Park | |
| 2021/0347048 A1 | 11/2021 | Trevor | |
| 2022/0088237 A1 | 3/2022 | Hauser | |
| 2023/0050980 A1 | 2/2023 | Zahdeh | |

OTHER PUBLICATIONS

Huang, Feixiang; Robotic Delivery System for Material Handling [Master's Thesis, University of Akron], Dec. 2014.

Int'l Application Serial No. PCT/US22/79883 Int'l Search Report and Written Opinion mailed Feb. 3, 2023.

Mobile Autonomous Robotic Cart 3 Series Overview, 3 Series Data Sheet v220301A, retrieved on Jul. 22, 2022, https://www.multechnologies.com/hubfs/manuals/MARC_3_Series_data_sheet_2203a.pdf.

Office Action (Final Rejection) dated Mar. 27, 2024 for U.S. Appl. No. 17/207,204 (pp. 1-18).

Office Action (Non-Final Rejection) dated Feb. 10, 2023 for U.S. Appl. No. 17/207,195 (pp. 1-18).

Office Action (Non-Final Rejection) dated Sep. 14, 2023 for U.S. Appl. No. 17/207,204 (pp. 1-21).

Office Action (Non-Final Rejection) dated Sep. 28, 2023 for U.S. Appl. No. 17/208,672 (pp. 1-15).

Office Action (Non-Final Rejection) dated Dec. 19, 2023 for U.S. Appl. No. 17/538,668 (pp. 1-31).

Office Action (Notice of Allowance and Fees Due (PTOL-85)) dated Mar. 4, 2024 for U.S. Appl. No. 17/208,672 (pp. 1-9).

Office Action (Notice of Allowance and Fees Due (PTOL-85)) dated Jun. 12, 2023 for U.S. Appl. No. 17/207,195 (pp. 1-8).

Office Action dated Mar. 27, 2024 for U.S. Appl. No. 17/207,204 (pp. 1-19).

Scholz, Jonathan et al; Cart Pushing with a Mobile Manipulation System: Towards Navigation with Moveable Objects, retrieved on Jul. 7, 2022, https://www.cs.cmu.edu/~maxim/files/cartplanner_icra11.pdf.

(56) References Cited

OTHER PUBLICATIONS

Wang, Ziyu; Autonomous Robotic Cart for Food Delivery on Airplane, [Master's Thesis, NYU Tandon School of Engineering], Fall 2017, retrieved on Jul. 22, 2022 http://engineering.nyu.edu/mechatronics/projects/MSprojects/2017-2018/4/report.pdf.

* cited by examiner

ROBOTIC SOCIAL INTERACTION

CROSS-REFERENCE TO RELATED APPLICATION

The present application claims priority under 35 U.S.C. 120 to U.S. Provisional Application No. 63/022,348 by Brooks et al., titled "A CLEANING ROBOT", filed May 8, 2020, and to U.S. Provisional Application No. 63/022,349 by Brooks et al., titled "ROBOTIC SOCIAL INTERACTION", filed May 8, 2020, both of which are hereby incorporated by reference in their entirety and for all purposes.

COPYRIGHT NOTICE

A portion of the disclosure of this patent document contains material which is subject to copyright protection. The copyright owner has no objection to the facsimile reproduction by anyone of the patent document or the patent disclosure as it appears in the United States Patent and Trademark Office patent file or records but otherwise reserves all copyright rights whatsoever.

TECHNICAL FIELD

The present disclosure relates generally to robotics, and more specifically to robotic social interaction.

DESCRIPTION OF RELATED ART

Robots are increasingly employed for performing a variety of tasks. However, many tasks otherwise capable of being completed by robots take place in environments in which humans are present. The presence of humans presents a significant problem for robotic solutions since humans behave in ways that are complex and difficult to predict. Accordingly, improved techniques for human-robot interaction are desired.

OVERVIEW

According to various embodiments, techniques and mechanisms described herein provide for systems, devices, methods, and machine readable media for robotic social interaction. A method may be implemented at a robot. The robot may autonomously traverse a physical environment along a first path from a first location to a second location via a mobility apparatus. The first path may be determined based on sensor data collected from a sensor module at the robot. The sensor data may characterize the physical environment. The robot may autonomously identify via a processor a human located within the physical environment. The robot may autonomously predict via the processor a second path along which the human is traversing the physical environment. The robot may autonomously determine via the processor that a predicted distance between the robot and the human falls below a designated threshold. The predicted distance may be predicted based on the first and second paths. The robot may determine via the processor a third path through the physical environment. The third path may end at the second location. The third path may be determined based on the second path so as to avoid the human. The robot may autonomously update the traversal of the physical environment from the first path to the third path.

In some implementations, the robot may determine a model of the physical environment based on the sensor data. The model may represent one or more surfaces within the physical environment. The model may be a three-dimensional model. The three-dimensional model may represent one or more stationary physical objects. The first and third paths may be determined to avoid the one or more stationary physical objects. Predicting the second path may involve identifying a first plurality of locations. Each of the first plurality of locations may be associated with a first respective point in time. The human may be present at each of the first plurality of locations at the first respective point in time. Alternatively, or additionally, predicting the second path further may involve determining a second predicted plurality of locations. Each of the second predicted plurality of locations may be associated with a second respective point in time. The human being may be predicted to be present at each of the second plurality of locations at the second respective point in time.

In some embodiments, the robot may autonomously clean a designated surface within the physical environment while traversing the physical environment along the first path. Cleaning may be halted when it is determined that the predicted distance between the robot and the human falls below the designated threshold. Cleaning the surface may involve autonomously positioning an ultraviolet light source in proximity with the designated surface. The ultraviolet light source may be coupled with a robotic arm. Positioning the ultraviolet light source in proximity with the designated surface may involve autonomously moving the robotic arm. The robot may autonomously resume cleaning the designated surface when it is determined that the human has moved away from the designated surface.

In some embodiments, the robot may include a communication interface facilitating autonomous communication with the human. The robot may identify a role associated with the human and/or determine a communication mode for communicating with the human based on the identified role. The sensor module may includes a camera. The sensor data may include image data. The human may be identified at least in part by analyzing the image data via the processor. The sensor module may include a depth sensor, the sensor data may include depth information, and predicting the second path may involve analyzing the depth information.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The included drawings are for illustrative purposes and serve only to provide examples of possible structures and operations for the disclosed inventive systems, apparatus, methods and computer program products for robotic cleaning solutions. These drawings in no way limit any changes in form and detail that may be made by one skilled in the art without departing from the spirit and scope of the disclosed implementations.

DETAILED DESCRIPTION

Figure 1:
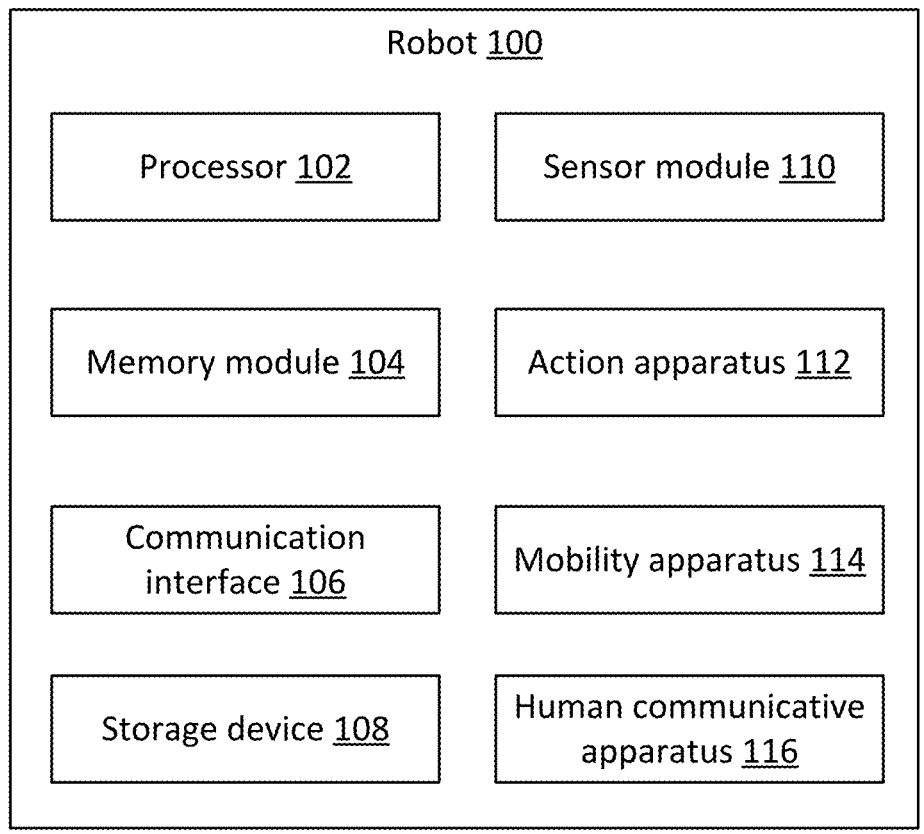
FIG. 1 illustrates an architecture diagram for a robot 100, configured in accordance with one or more embodiments.

Techniques and mechanisms described herein are directed to a robot capable of making decisions and taking actions based on social accommodation and prediction of human and non-human activity. The robot may be equipped with a movement capability and may execute a task such as cleaning, monitoring, or object manipulation within a physical environment. At the same time, the robot may actively scan the environment to distinguish people and animals from objects and surfaces. The robot may then predict the actions of people and/or animals and respond accordingly.

In some implementations, the robot may be guided in its activity based on communication with a remote computing device such as a control computer having access to a database system. Alternatively, or additionally, the robot may report its actions to such a system.

In some implementations, the robot may coordinate with other robots. The other robots may be configured to perform complementary activities or may be focused on other tasks. Each robot may be directed by a central command and control apparatus. Alternatively, or additionally, the robots may communicate with each other directly.

In some implementations, the robot may communicate with nearby people. For example, the robot may receive instructions from a nearby person. As another example, the robot may receive instructions about social accommodation from a nearby person. The robot may be configured to verify the authority of the person to issue such instructions. For instance, the robot may be configured to ascertain the person's identity and/or role through any of various authentication mechanisms.

In some implementations, a robot may be equipped with semantic perception. Semantic perception may allow a robot to not only sense the presence of surfaces and objects in an environment, but also to identify the characteristics of those surfaces and objects. For example, people may be identified as such, and actions may be taken based on their anticipated behavior.

In some implementations, a robot may be equipped with multimodal perception. Multimodal perception may allow the robot to combine multiple approaches at the same time, for instance by performing one or more of sensing, movement, reporting, and/or social accommodation activities simultaneously or in close temporal proximity. Alternatively, or additionally, multimodal perception may allow the robot to combine input from different sensors such as one or more internal or remotely accessible microphones, cameras, gyroscopes, or other detecting devices. Accordingly, a robot may be equipped to conduct the flexible handling of objects, to develop and execute socially appropriate plans for interacting with an environment, and to adapt to new environments.

In some implementations, social accommodation allows a robot to treat humans differently than objects, allowing more natural and socially appropriate behavior. Velocity and trajectory information for humans can be used, allowing a robot to plan for where they are likely to be, and not merely where they are now. In addition, a robot can signal to humans in various ways to help alert humans to the current and future behavior of the robot.

In some implementations, a robot may be equipped to identify, create, and use two-dimensional (2D) and/or three-dimensional (3D) maps. For example, a robot may map annotations of regions such as aisles and departments in a store. As another example, the robot may perform continuous maintenance of maps over time. As yet another example, the robot may identify corridors and preferred routes for navigation, for instance based on past experience. Dynamic objects may be handled separately from fixed objects, and humans may be tracked based on fusing information from multiple sensors.

In particular embodiments, a robot can also perform tasks in a socially aware way, for instance by recognizing individuals based on role and/or identity, and then treating individuals differently based on those roles and/or identities. For example, a robot in a hospital setting may place a very high priority on avoiding doctors and nurses, who may be in a hurry to provide medical services. As another example, the robot may be configured to respond to instructions from maintenance workers and administrators. However, the robot may be less accommodating of other individuals, such as members of the general public.

FIG. 1 illustrates an architecture diagram for a robot 100, configured in accordance with one or more embodiments. According to various embodiments, the robot 100 may be configured in a variety of form factors. The robot 100 includes a processor 102, a memory module 104, a communication interface 106, a storage device 108, a sensor module 110, an action apparatus 112, a mobility apparatus 114, and a human communicative apparatus 116.

According to various embodiments, the robot 100 may include one or more processors 102 configured to perform operations described herein. The memory module 104 may include one or more transitory memory elements, such as random access memory (RAM) modules. The storage device 108 may be configured to store information such as computer programming language instructions and/or configuration data.

In some implementations, the robot 100 may include one or more communication interfaces 106 configured to perform wired and/or wireless communication. For example, the communication interface 106 may include a WiFi communication module. As another example, the communication interface 106 may include a wired port such as a universal serial bus (USB) port, which may be connected when the robot couples with a docking or charging port or device.

According to various embodiments, the sensor module 110 may include one or more of various types of sensors. Such sensors may include, but are not limited to: visual light cameras, infrared cameras, microphones, Lidar devices, Radar devices, chemical detection devices, near field communication devices, and accelerometers.

In particular embodiments, the sensor module 110 may communicate with one or more remote sensors. For example, an environment may be equipped with one or more of various types of sensors, data from which may be relayed to robots within the vicinity.

According to various embodiments, the action apparatus 112 may be any one or more devices or components used to perform a task. Such devices may include, but are not limited to: robotic arms, other types of manipulators, chemical applicators, light sources, and sensors.

According to various embodiments, a device may be attached to the robot 100 in any of various ways. For example, the device may be attached in a fixed orientation relative to a robot drive mechanism. As another example, the device may be attached to the robot via a robotic arm having any of a variety of possible geometries.

According to various embodiments, the mobility apparatus may include one or more of any suitable mobility devices. Such devices may include, but are not limited to, one or more motorized wheels, balls, treads, or legs. In some configurations, the mobility apparatus may include one or more rotational and/or gyroscopic elements configured to aid in mobility and/or stability.

According to various embodiments, the robot may communicate directly with a human via the human communicative apparatus 116. The human communicative apparatus 116 may include one or more components for conducting visible and/or audible communication with a human. For instance, the human communicative apparatus 116 may include one or more display screens, LEDs, motors, robotic arms, motion sensors, speakers, microphones, or other such components. For example, the human communicative apparatus 116 may include a display screen coupled with a motor that may be used to provide visual cues about the robot's activities.

In particular embodiments, the robot 100 may be configured to communicate directly or indirectly with other robots in order to accomplish its tasks. For example, robots may share information to build up an accurate model of an environment, identify the location and/or trajectory of humans, animals, or objects, perform social accommodation. As another example, robots may coordinate to execute a plan. For instance, one robot may be interrupted in a task due to social accommodation. The robot may then move on to another task, while a different robot may then later perform the interrupted task. As yet another example, robots may coordinate to perform a single task.

Figure 2:
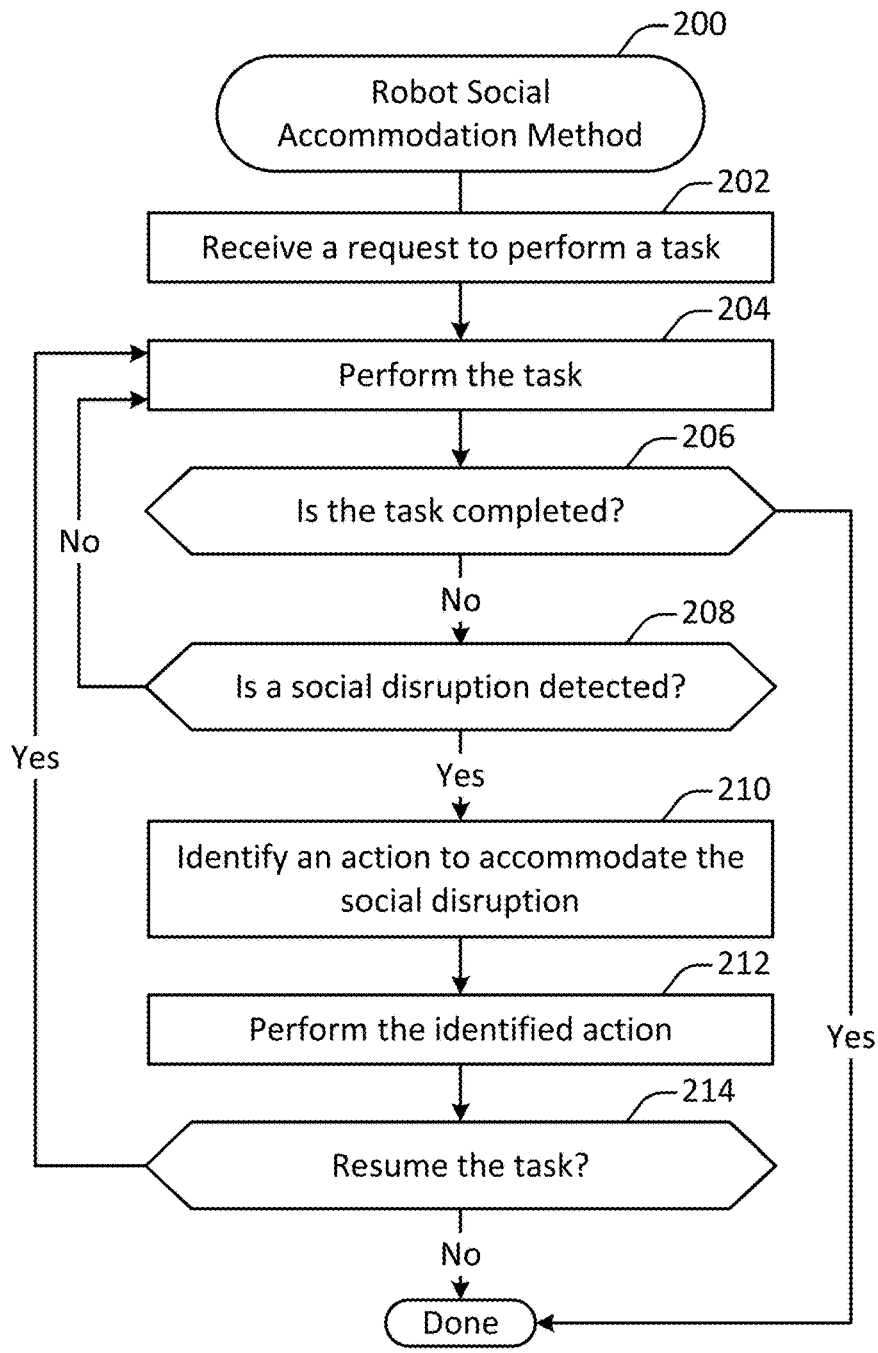
FIG. 2 illustrates a method 200 for social accommodation by a robot, performed in accordance with one or more embodiments.

FIG. 2 illustrates a method 200 for social accommodation by a robot, performed in accordance with one or more embodiments. The method 200 may be performed by the robot as part of, or in addition to, the execution of any other operations.

A request to perform a task is received at 202. According to various embodiments, the task may include any operation capable of being performed by the robot. For example, the task may include cleaning an object or surface, waiting at a designated location, or any of the actions discussed with respect to operation 210 as being performed to accommodate a social disruption.

The task is performed at 204. A determination is made at 206 as to whether the task is completed. If the task is completed, then the method is finished. If the task is not completed, then a determination is made at 208 as to whether a social disruption is detected. An action to accommodate the social disruption is identified at 210, and the action is performed at 212. A determination is made at 214 as to whether to resume the task. Depending on the outcome of that determination, the task is resumed at 204 or the method is terminated. When the method is terminated, the robot may move on to the next task.

According to various embodiments, the detection of a response to social disruption may be pre-configured and/or dynamically determined based on a variety of characteristics such as the environment in which the robot is operating, the identity or role of a human associated with the social disruption, the urgency of the robot's tasks, instructions received from a human, and/or one or more safety considerations.

Although a variety of specific examples are discussed herein, various configurations are possible. For example, some embodiments discussed herein refer to a robot configured to clean surfaces or objects, for instance via a UV light source capable of being positioned near to a surface or object. However, a robot may response to social disruption when performing any of a variety of tasks.

In some implementations, a robot may be interrupted while cleaning a door handle by a person walking up behind the robot. In such a situation, the robot may predict that the human is likely to proceed through the door. Accordingly, the robot may stop cleaning and move out of the way. If the human proceeds through the door, then the robot may restart the cleaning process from the beginning because the human may have touched the door handle. If the human walks away without proceeding through the door, then the robot may resume the cleaning process without starting from the beginning.

In some implementations, a robot may be interrupted while cleaning a door handle by the door handle turning or the door opening from the other side. In such a situation, the robot may predict that a human is likely to use the door, even if no human has been specifically detected. Accordingly, the robot may stop cleaning and move out of the way, and resume cleaning once the door has been closed and no people are detected in close proximity. While waiting, the robot may monitor the door handle to determine if it is touched.

In some implementations, a robot may be interrupted while cleaning a table by people who sit at the table. In such a situation, the robot may cease cleaning the table and move on to the next task.

In some implementations, a robot may be interrupted while cleaning a faucet at a sink by a person who moves near the robot. In such a situation, the robot may cease cleaning and move out of the way. The robot may then observe whether the person touches any objects or surfaces such as a sink or faucet. When the person is gone, the robot may resume its task. If the person touched a surface or object, the robot may restart the cleaning process for that surface or object.

In some implementations, when a task is interrupted, the robot may wait either passively or actively. If passively waiting to resume a task, the robot may select a spot off to the side from the predicted paths along which people are most likely to walk. If actively waiting to resume a task, the robot may select another task to perform. For example, if interrupted while cleaning a door knob, the robot may clean a different surface while it waits to resume cleaning the door knob. As another example, if interrupted while cleaning a faucet at a sink, the robot may move to a different faucet at a different sink.

In some implementations, a social disruption may constitute the actual movement of a human into close proximity with the robot. Alternatively, or additionally, a social disruption may constitute the predicted movement of a human into close proximity with the robot. For instance, a robot engaged in a cleaning task may sense its environment and predict that a human is moving along a path that will bring the human in close proximity to the robot. If so, the robot may treat the human's movement as a social disruption even though the human is not yet actually located proximate to the robot.

In some implementations, a robot may determine whether or not to wait and resume a task or move on to another task based on, for instance, predicted human activity. For example, the robot may predict that a human is likely to enter and quickly leave an area based on the human's movement along a path. In such a situation, the robot may elect to wait for the human to pass and then resume the task. As another example, the robot may predict that a social disruption is likely to be long-lasting, such as when a human sits down at a table. In such a situation, the robot may elect to move on to a different task.

According to various embodiments, the robot may strategically determine whether to employ active or passive waiting based on factors such as whether the area is crowded with people, the time required to switch between tasks, the time scheduled in which to complete one or more tasks, and/or instructions from humans.

According to various embodiments, as part of responding to a social disruption or at any other time, a robot may provide any of a variety of social cues. Examples of such cues may include, but are not limited to: lights, sounds, vibration, and movement. For example, a robot may activate one or more lights and/or emit one or more sounds when cleaning is initiated. As another example, the robot may activate a spinning mechanical component to provide a visual indicator associated with cleaning.

In particular embodiments, the robot may employ a human communicative apparatus, as discussed with respect to FIG. 1, to execute complex human interactions. For example, a robot may be equipped with a display screen that is coupled with one or more motors. When the robot is actively engaged in ultraviolet cleaning of a surface such as a keyboard, the display screen may display a simulated face. The face may include a visual feature such as sunglasses to indicate that bright light is being emitted by the ultraviolet light source. The motors may be activated to position the display screen so that the face appears to be looking toward the ultraviolet light source, so as to provide a visual cue about the location of the ultraviolet light source via a gaze direction. In addition, the ultraviolet end effector on which the ultraviolet light source may be equipped with one or more visible spectrum lights that are activated during cleaning, which may provide an additional visual cue indicating that ultraviolet light is being emitted. When a human approaches the robot, the robot may take one or more steps to respond. For example, the robot may disable the ultraviolet and visible light sources to show that cleaning has stopped. As another example, the robot may reposition the display screen so that the simulated face appears to gaze at the human, which provides a visual cue that the robot is aware of the human's presence. As yet another example, the robot may change the appearance of the display screen, for instance by removing the sunglasses, presenting a warning symbol and/or message, removing the sunglasses from the simulated face, and/or changing the facial expression displayed on the simulated face. When the human moves away from the robot, the robot may then return the display screen and other components of the human communicative apparatus to the previous state during which cleaning was conducted.

In particular embodiments, a robot may emit a visual social cue indicating how long a task will take. For example, a robot may be equipped with a visible screen that is configured to display one or more countdown clocks. A countdown clock may indicate a time remaining for cleaning a specific surface or object. Alternately, or additionally, a countdown clock may indicate a time remaining for cleaning an entire area. As another example, a robot may be equipped with one or more colored lights to indicate the degree of completion of a task. For instance, presenting a visual cue may involve changing the color of an LED strip. The visual social cue may be perceivable from a distance so that a human can decide whether to interrupt the robot.

In some embodiments, presenting a visual cue may involve emitting audio. For example, one or more sound effects may be emitted when people transition across virtual boundaries. As another example, audio communication may be emitted in the form of music. As yet another example, audio communication may be emitted in the form of spoken natural language, for instance via text to speech or voice recording. Natural language communication may be presented on a display screen, or through speech, or a combination thereof. As still another example, the robot may emit a tune or whistle to indicate its progression in a task. As still another example, the robot may be configured to emit a verbal countdown or other natural language descriptions of progress along a task. For instance, the robot may state a task and verbally identify the initiation and/or completion of a task.

In some embodiments, presenting a visual cue may involve an information screen configured to display information such as text or icons. For instance, a caution icon may be displayed.

In some embodiments, presenting a visual cue may involve a projector to display information similarly to screen displays. Alternatively, or additionally, a projector may present a visual cue through illumination based on color and/or brightness similarly to LED strips. A projector may be used to show a graphic and/or text on the ground, for instance to indicate a safe boundary for humans to stay away, or onto a surface being disinfected, for instance to display AR information.

In some embodiments, a display screen on the robot may display an emotionally expressive face that is used for indicating system states. For example, when people are detected, the robot may present a happy face. As another example, when people are engaged in interaction for communicating with the robot, the robot may present a face that reflects the situation or statement (e.g., happy, apologetic, or thankful). As yet another example, when the robot predicts that people may soon be in an unsafe location, the robot may display a face indicating shock or panic.

In some embodiments, presenting a visual cue may involve motion. For example, the robot may use its arm for communicative gestures such as pointing to objects or surfaces for confirmation or socially communicating with people, for instance by waving. As another example, the robot may have the ability to move a "head" area (e.g., with 1-3 degrees of freedom) on which a display screen is mounted to control head gaze for communicating with people and directing sensors. Head gaze direction may be used to communicate task state (e.g., navigational goals, object/surface targets for disinfection) or interaction state (e.g., people being interacted with). Neck motions may also be used as communicative gestures, such as shaking the head no. As yet another example, the robot may use a mobile base trajectory for communication, for instance by driving to encircle a region to refer to it for task confirmation. As still another example, any of the robot's movable components may be used for emphasis within a communicative message, for instance for beat gestures.

In particular embodiments, the method 200 may include one or more operations not shown in FIG. 2. For example, the robot may log or report a social disruption, an action performed in response to the social disruption, and/or the robot's success or failure at performing the requested task.

Figure 3:
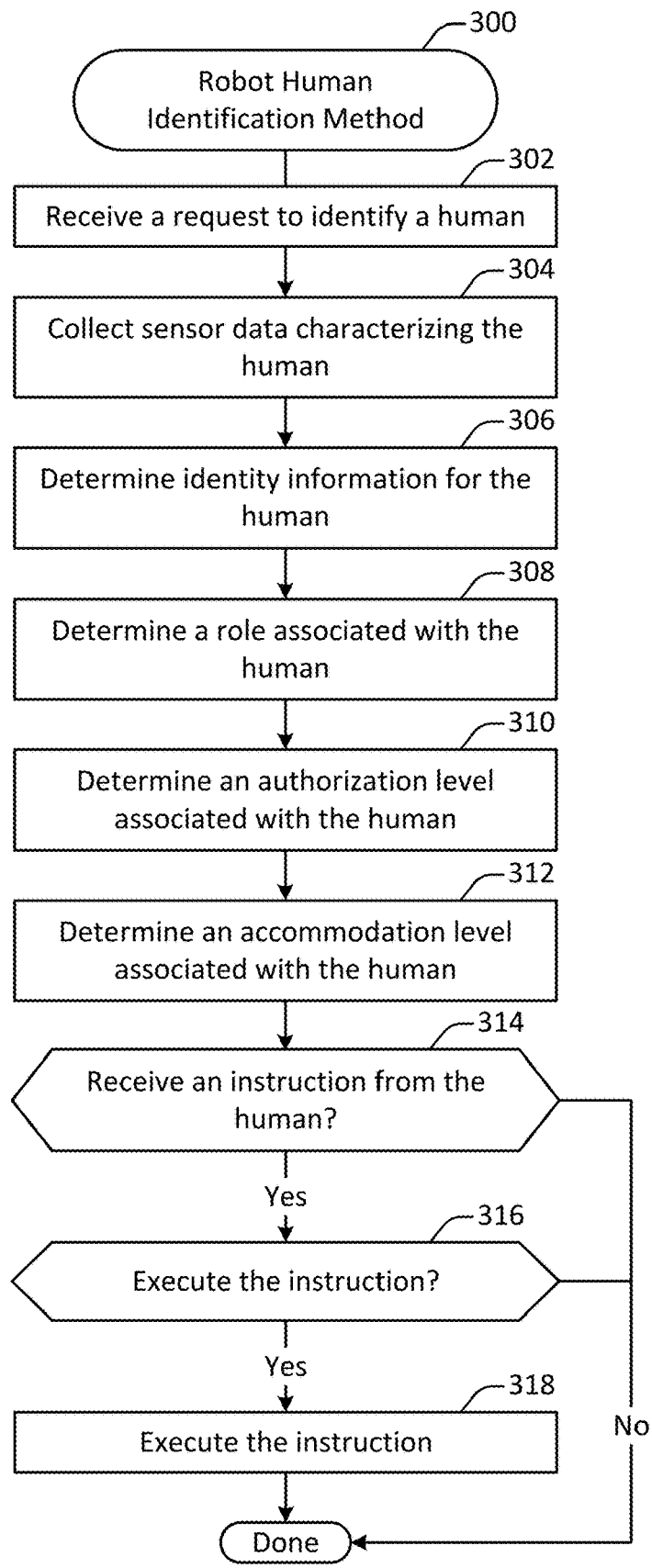
FIG. 3 illustrates a method 300 for human identification by a robot, performed in accordance with one or more embodiments.

FIG. 3 illustrates a method 300 for human identification by a robot, performed in accordance with one or more embodiments. The method 300 may be performed by the robot as part of, or in addition to, the execution of any other operations. For example, the method 300 may be performed by the robot as it is navigating an environment, performing social accommodation, and/or executing a task. As another example, the method 300 may be an example of a social disruption as discussed with respect to the operations 208, 210, 212, and 214 in the method 200 shown in FIG. 2.

A request to identify a human is received at 302. According to various embodiments, the request may be generated automatically, for instance whenever a human comes within a designated range of the robot. Alternatively, or additionally, the request may be generated when an event is detected. For instance, the request may be generated when a human instructs the robot to perform a task.

Sensor data characterizing the human is collected at 304. According to various embodiments, various types of sensor data may be collected. For example, visual data such as video footage and/or one or more still images may be collected from a camera. As another example, an RFID sensor, barcode, or other such data may be read from an ID badge associated with the human.

When possible, identity information for the human is determined at 306. In some implementations, the identity information may be determined at least in part by querying a remote database. For example, an image of a human may be used to query a remote database that links such images with information such as name and role. As another example, an ID barcode or RFID code may be used to query such a database.

A role associated with the human is determined at 308. In some embodiments, when available, the role may be determined directly from the identity information determined at the operation 306. Alternatively, or additionally, role information may be determined based on contextual cues. For example, a doctor or nurse in a hospital setting may be identified based on the presence of clothing or medical equipment. As another example, an employee or manager in an office, industrial, or retail setting may be identified based on clothing or insignia. As yet another example, individuals having a particular role may carry a special identifier such as an RFID tag on a badge.

An authorization level for the human is determined at 310. In some implementations, the authorization level may characterize the type of instructions that the human is authorized to give to the robot. For instance, a robot may be configured to act on any instructions from a designated maintenance operator. At the same time, the robot may be configured to act on a limited set of instructions from authorized persons such as doctors and nurses in a hospital, employees in an office setting, or managers in an industrial setting. The robot may be configured to ignore instructions from unauthorized individuals.

An accommodation level associated with the human is determined at 312. According to various embodiments, the accommodation level may indicate a level of deference afforded to the human. For example, in a hospital setting, the robot may be configured to give doctors and nurses a wide berth, while affording less deference to the general public.

At 314, a determination is made as to whether an instruction is received from the human. At 316, if an instruction is received, a determination is made as to whether to execution the instruction, for instance based on the human's authorization level. If the decision is made to execute the instruction, then at 318 the instruction is executed.

According to various embodiments, the instruction could be any instruction within the robot's command set. For example, the human could instruct the robot to start or stop cleaning an area. As another example, the human could instruct the robot to move or stop moving. As yet another example, the human could instruct the robot to pause a task.

According to various embodiments, the robot may be configured to receive user input in any of a variety of ways. For example, a human may employ natural language to command the robot. Voice input may be provided to a microphone located on the robot, and/or through voice or typed text on a mobile phone, web application, or desktop application.

In some implementations, the robot may be configured to receive user input via hand gestures, for instance to facilitate contact-less interaction in noisy environments where speech recognition may be less accurate. Such gestures may be used for operations such as engaging or disengaging the robot, instructing it to start or stop tasks, providing yes or no answers, navigating a menu associated with the robot, pointing at regions or objects in the real world, making movements relative to a screen displaying visual information, or a variety of other gestures.

In some implementations, user input with the robot may be provided based on a remote user interface, for instance via a mobile phone, web application, or desktop application. In this way, a user may instruct and communicate with the robot when not co-present with it. Such interaction make take place via a graphical user interface, via spoken voice commands (e.g., a voice-based phone call), via a video call, or a combination thereof. When a user is co-present with the robot, information from a mobile device may be referenced during face-to-face interaction, and the mobile device used as an additional input device.

In some implementations, user input with the robot may be provided via near-field communication. For example, a user may authenticate or provide other information via an RFID badge.

In particular embodiments, touch-based user input may be used. Examples of such input may include, but are not limited to, touching options on a screen, pressing buttons, or activating touch sensors. For example, the robot may have capacity and/or resistive touch sensors on the surface of its body. As another example, the robot may have torque sensing at joints, which may help to detect contact for a variety of reasons (e.g., safety).

Figure 4:
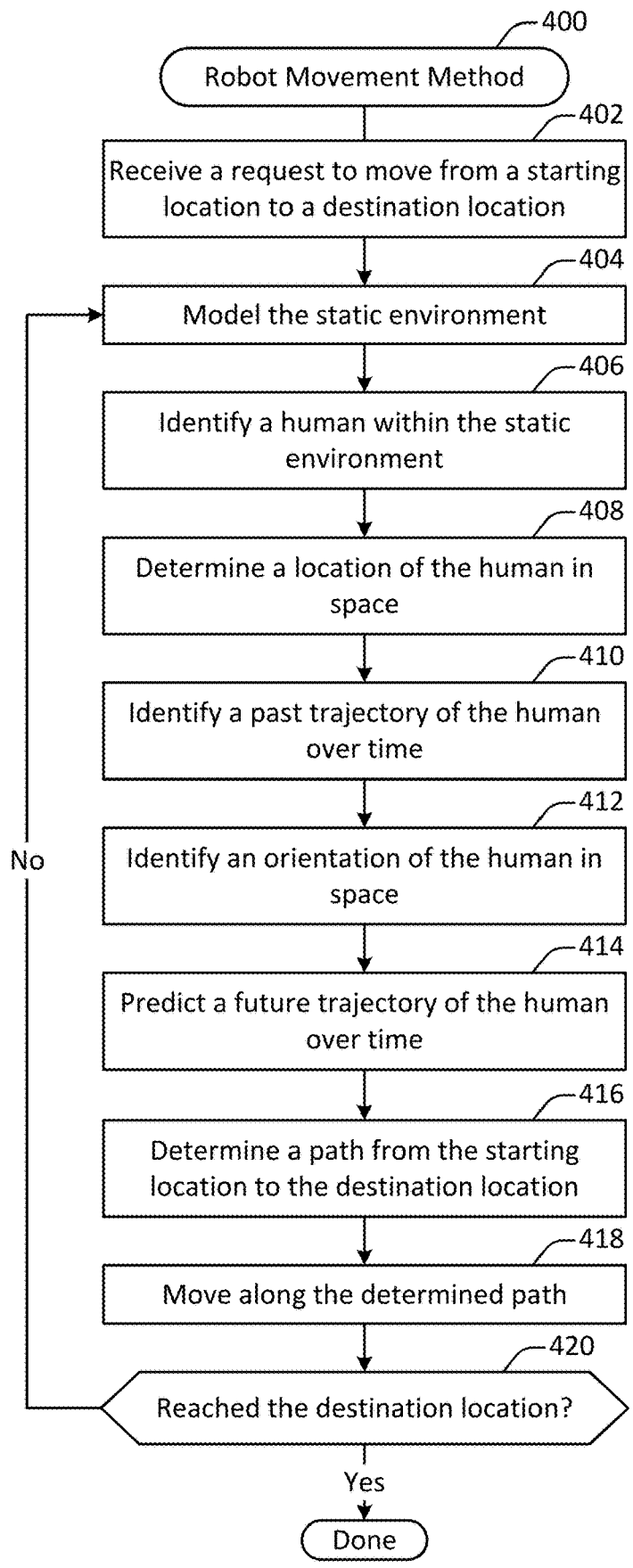
FIG. 4 illustrates a method 400 for moving a robot, performed in accordance with one or more embodiments.

FIG. 4 illustrates a method 400 for moving a robot, performed in accordance with one or more embodiments. The method 400 may be performed in order to position the robot for performing a task. Alternatively, or additionally, the method 400 may be performed to move the robot to a location where it does not interfere with human activity. As still another example, the method 400 may be performed while the robot is performing a task, such as monitoring an area.

A request to move from a starting location to a destination location is received at 402. According to various embodiments, the destination location may be determined based on any of a variety of considerations. For example, the robot may receive an instruction to move to a designated location. As another example, the robot may determine the location based on a task or set of tasks that the robot is attempting to perform.

The static environment is modeled at 404. In some implementations, the static environment may be modeled based on sensor data received from one or more of a visible light camera, an infrared camera, a depth sensor, radar, lidar, or any other suitable sensor. The model of the static environment may indicate features such as walls and/or fixed objects such as tables.

In particular embodiments, information about the static environment may be predetermined. For instance, a robot may be provided with a two-dimensional or three-dimensional map of an environment.

In particular embodiments, information about the static environment may be received from a remote data source. For example, one or more sensors in an environment, such as sensors located on another robot, may collect information about the environment. Such information may then be transmitted to the robot, which may use the information to replace or supplement locally collected information.

A human within the static environment is identified at 406. The human may be identified by performing object recognition, for instance via pre-trained neural networks, on the sensor data.

In some embodiments, a human may be identified at least in part by scanning an environment with a sensor having limited capabilities. For example, radar or lidar may be used to detect objects that may or may not be humans. As another example, a laser may scan the room, for instance at a few inches from the ground to identify objects that may or may not be humans. Such sensors may provide limited information, such as a distance from the robot to an object in a particular direction. However, a pattern in the distance in a particular direction may be recognized as potentially indicating the presence of a human.

Figure 6:
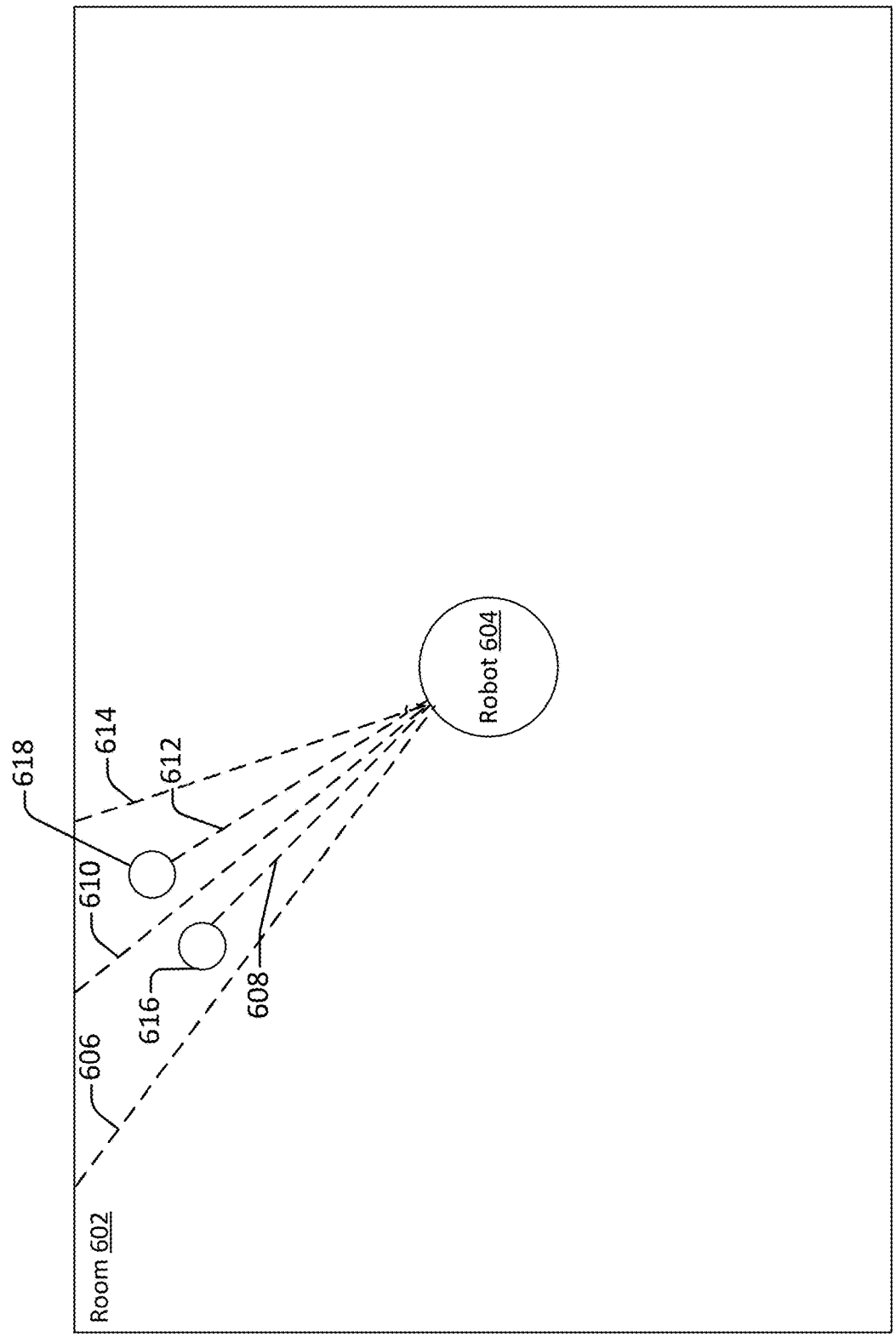
FIG. 6 illustrates a diagram generated in accordance with one or more embodiments.

Examples of such an approach are shown in FIG. 6, which illustrates a diagram generated in accordance with one or more embodiments. FIG. 6 presents a top-down view of a room 602. In FIG. 6, a robot 604 is located within the room 602. The robot scans its environment with a two-dimensional laser positioned along a plane a few inches above the ground. This scanning process allows the robot to determine a distance from the robot to the nearest obstacle in various directions. Examples of the laser depth detection values are shown at 606, 608, 610, 612, and 614. The laser beams at 606, 610, and 614 all return distances consistent with the wall of the room. However, the laser beams at 608 and 612 return shorter distances due to the obstacles at 616 and 618. From the number and shape of these obstacles, the robot may determine that they may correspond to a person's legs. According to various embodiments, a similar technique may be used to identify objects as candidates for wheelchairs, animals, crawling babies, and other such obstacles.

In particular embodiments, the technique illustrated in FIG. 6 may be employed by a sensor other than a laser. For example, binocular vision may be used to determine a depth from the robot to an obstacle in a similar fashion. An example of such a technique is shown in FIG. 7.

Figure 7:
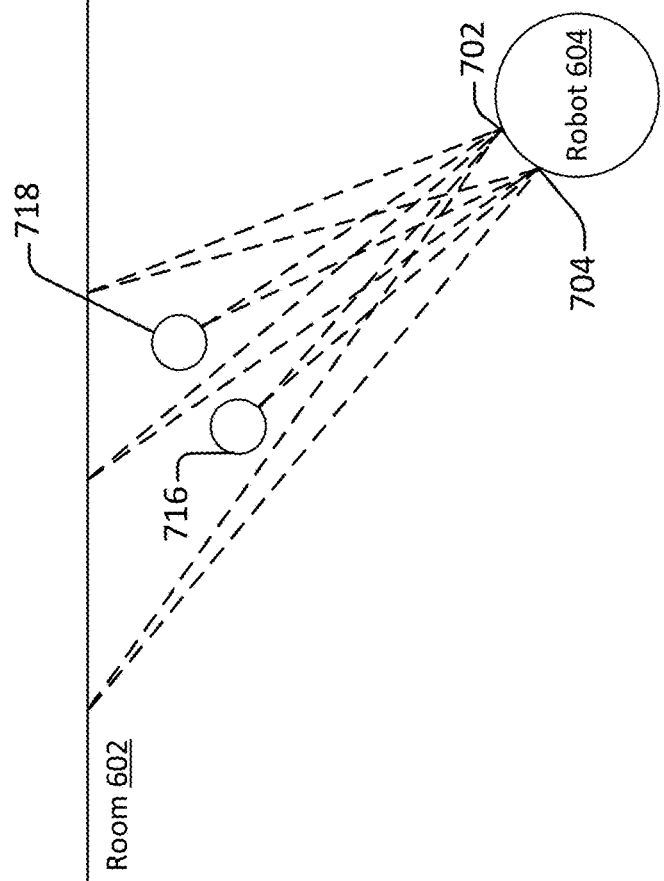
FIG. 7 illustrates a diagram generated in accordance with one or more embodiments.
Figure 8:
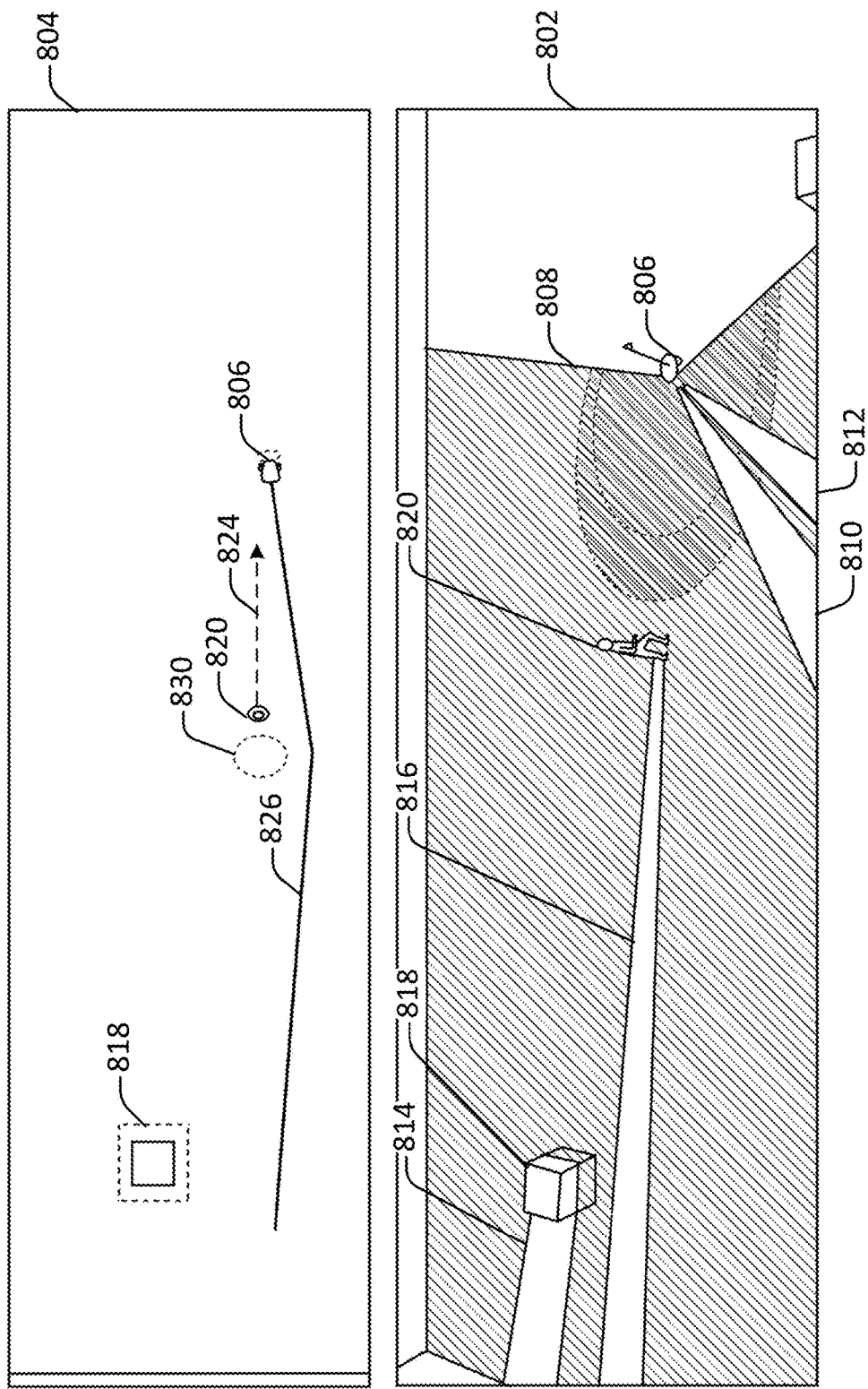
FIG. 8, FIG. 9, FIG. 10, and FIG. 11 illustrate diagrams generated in accordance with one or more embodiments.

FIG. 7 illustrates a diagram generated in accordance with one or more embodiments. FIG. 7 presents a top-down view of the room 602. In FIG. 7, the robot 604 observes its environment with sensors located at 702 and 704 and positioned along a plane a few inches above the ground. Together these two sensors can determine a location for the objects 716 and 718 because each of the sensors views the objects from a different perspective.

In some implementations, an object identified as a candidate by a sensor having limited capabilities, such as a two-dimensional laser depth sensor, may then be subjected to a more comprehensive analysis, such as one or more cameras. For instance, one or more sensors such as cameras may be used to capture monocular visual data, binocular visual data, or other visual data of the object. Such cameras may be equipped with sophisticated features such as pan and tilt, which may be used to focus on an object identified by the less sophisticated sensors. Then, an object recognition procedure may be used on the captured data to confirm whether the object is a person and to determine various information about the person, such as the person's role or identity.

In particular embodiments, a sensor may combine active depth and passive optical sensing capabilities. For example, a camera may include a projected structured infrared light component that projects a pattern of infrared light onto the surroundings, which may be used to determine distance from the camera to the objects. As another example, a camera may include depth detection based on time-of-flight of projected infrared light. In either case, the same camera may also detect visible light.

In particular embodiments, once an object is identified as a person, the person may be subject to more refined identification in which the person is identified. As discussed with respect to the method 300 shown in FIG. 3, a human may be identified in various ways.

In particular embodiments, a human may be classified based on age, size, a number of times that the human previously has been observed, or any other characteristics. The human may then be treated differently based on the human's past interactions with the robot. For example, a human who has never been observed may be given a relatively wide berth because the robot may be unfamiliar to the human. As another example, a child may be given a relatively wide berth. As another example, a human who is identified as having been near the robot many times in the past may be given a relatively narrow berth since the robot is likely familiar to the human.

A location of the human in space is determined at 408. In some implementations, the human may be positioned in a virtual two-dimensional or three-dimensional map of the environment. The human may be located in space by using information captured by one or more depth sensors, optical sensors, laser sensors, lidar sensors, and/or other sensors. Positioning the human in space may allow the robot to reason about the human, for instance for the purpose of trajectory mapping and/or route planning.

A past trajectory of the human over time is identified at 410. According to various embodiments, the past trajectory of the human over time may be identified by analyzing historical sensor data. For example, data from a two-dimensional laser scanner over time may be used to plot the location of the human over time in the virtual two-dimensional or three-dimensional map of the environment. As another example, video data from one or more cameras may be used for tracking people or objects.

An orientation of the human in space is determined at 412. In some implementations, the orientation may characterize the position of the human as standing, sitting, kneeling, or arranged in some other position. Alternatively, or additionally, the orientation may characterize the position of the human as facing in a particular direction relative to the environment.

In particular embodiments, the orientation may be determined based at least in part on the past trajectory of the human. For example, if the human is moving along a trajectory, the human may be presumed to be facing in the direction of the trajectory.

In particular embodiments, the orientation may be determined based at least in part on other physical objects. For example, if the human is sitting in a chair, the orientation may be determined at least in part by the position of the chair.

Movement of the identified humans within the static environment is predicted at 414. According to various embodiments, movement of humans may be predicted via heuristics. For example, if a person opens a door, the person is likely to move through the door in the near future. As another example, when a small group of people are positioned near one another and talking intensely, they are likely to continue talking unless one of the principals has intimated through gesture, spoken words, or body motion that they are leaving. As yet another example, when a person makes a gesture such as a "come through" wave, the robot may predict that the person is waiting for the robot to move. In such a situation, the robot may proceed and may make a social acknowledgement of the person's action. Such a social acknowledgement may include a message on a screen, a light, a spoken message, or another audible notification.

In some implementations, movement of humans may be predicted via past actions. For example, the robot may have observed in the past that a particular human tends to follow a particular path through a space. As another example, the robot may identify a person's likely trajectory based on the person's role. For instance, the robot may expect a maintenance worker to enter a particular door, which may never be entered by members of the public.

A path from the starting location to the destination location is determined at 416. The robot moves along the determined path at 418. According to various embodiments, the robot may give a wide berth to people whenever possible, based on the predicted path of each person. For example, the robot may determine a path to the destination that minimizes travel time while at the same time staying at least 6 feet from each person when in an open area. In a more closed area such as a hallway in which less room is available, the robot may plan the path so as to stay as far from each person as possible. In general, the robot may plan a path in such a way as to avoid requiring humans to alter their activities to accommodate the robot. The robot may alter both its path and its speed in order to enforce this distancing.

In particular embodiments, the robot may alter its path based on the identity of the person. For example, the robot may determine a path that places it relatively further from people who it has not encountered before, even if such a path is longer than necessary. Such people are unknown to the robot, and the robot may be unknown to such people, rendering the actions of such people less predictable than people who have interacted with the robot before. As another example, the robot may determine a path that places it relatively further from small children or animals even if such a path is longer than necessary since animals and small children may be inherently unpredictable. As yet another example, the robot may determine a path that places it relatively further from humans whose behavior the robot cannot accurately predict. Such people may include, for instance, maintenance workers moving rapidly between surfaces in a space, doctors moving from patient to patient in a hospital setting, or children playing.

A determination is made at 420 as to whether the destination location has been reached. If not, the routine may continue until the destination is reached. That is, the robot may continue to model the environment and the location of people to execute the movement in a socially appropriate manner.

According to various embodiments, the techniques described in FIG. 4 may be used to move the robot relative to any or all of a variety of obstacles. For example, although the method 400 is described with respect to moving a robot to a destination when a single human is present, the techniques may be applied to environments in which any number of humans are present. As another example, the method 400 may be applied to move the robot to a destination in which an environment includes one or more animals.

In some implementations, the method 400 may be applied to move the robot to a destination in which an environment includes one or more movable inanimate objects, such as other robots. The movement of objects that are not self-directed may be predicted via a physics-based simulation. For example, a ball that is bouncing or rolling down a hill may be predicted to continue bouncing or rolling down a hill. The movement of robots may be predicted at least in part based on communication with those robots. Alternatively, or additionally, robots may be modeled in a manner similar to humans.

FIGS. 8 through 11 illustrate diagrams generated in accordance with one or more embodiments. The diagram 802 illustrates a perspective view of an environment, while the diagram 804 illustrates a top-down view of the same environment. One or more such views may be generated by the robot 806 as it collects information about a physical space. A two-dimensional, top-down view such as the view 804 may allow the robot 806 to reason about its environment, for instance to determine a path to reach an objective.

According to various embodiments, the robot's field of view according to one or more depth sensors is illustrated by the shaded region 808. The depth sensors may operate in two or more dimensions and may indicate the robot's proximity to the nearest visual obstacle. The robot cannot directly observe the regions 814 and 816 since those regions are blocked by the box 818 and the person 820.

The regions 810 and 812 represent an active scan of the robot's environment, for instance using cameras. Visual data may be used to perform tasks such as object recognition, person identification, or identification of obstacles that are located on a plane different from two-dimensional depth sensors.

The robot 806 is attempting to navigate to the point 822 in the environment. However, the most direct path to the point 822 is blocked by the person 820, who is walking through the environment. The person's most recent position according to sensor data is illustrated at 830. Accordingly, the robot may predict a projected trajectory 824 for the person 820 and then determine a path 826 that avoids the person. The path 826 may be determined to, at a minimum, avoid collision with the person 820. In some configurations, the path may be determined to avoid collision with the person 820 by a minimum distance. For instance, the robot may determine a path to the point 826 that is the shortest path that avoids putting the robot within three feet of the person 820.

Figure 9:
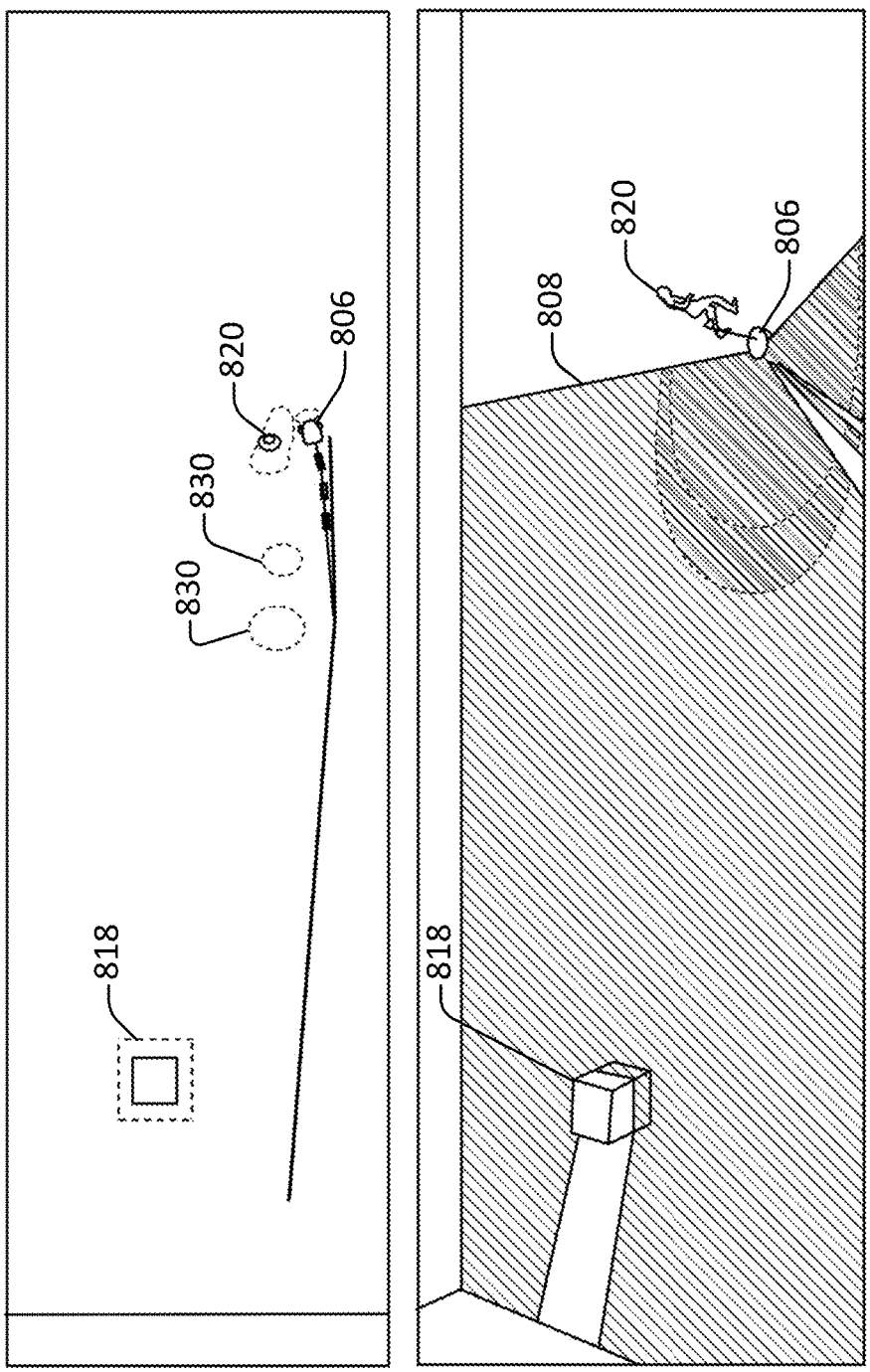
Figure 10:
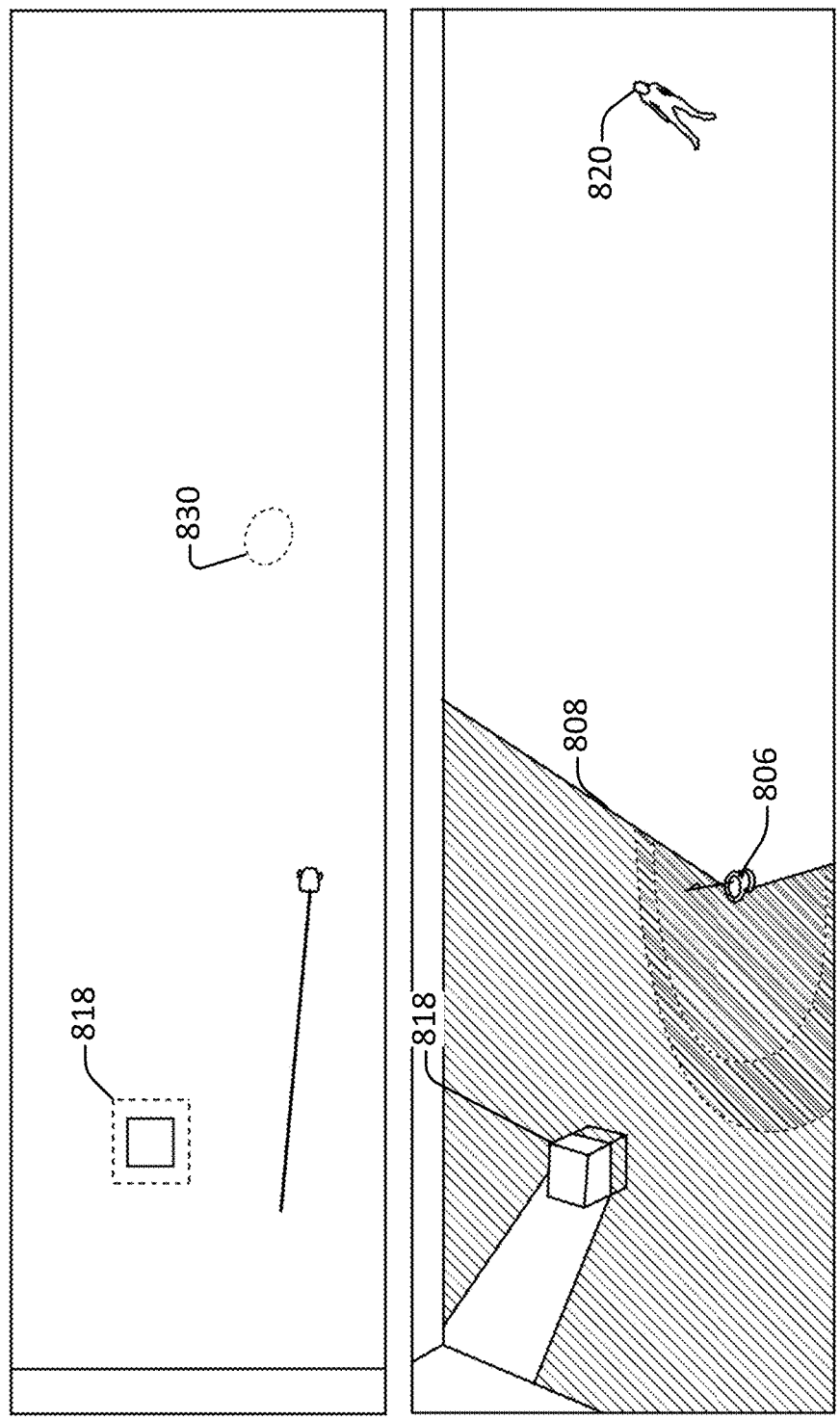
Figure 11:
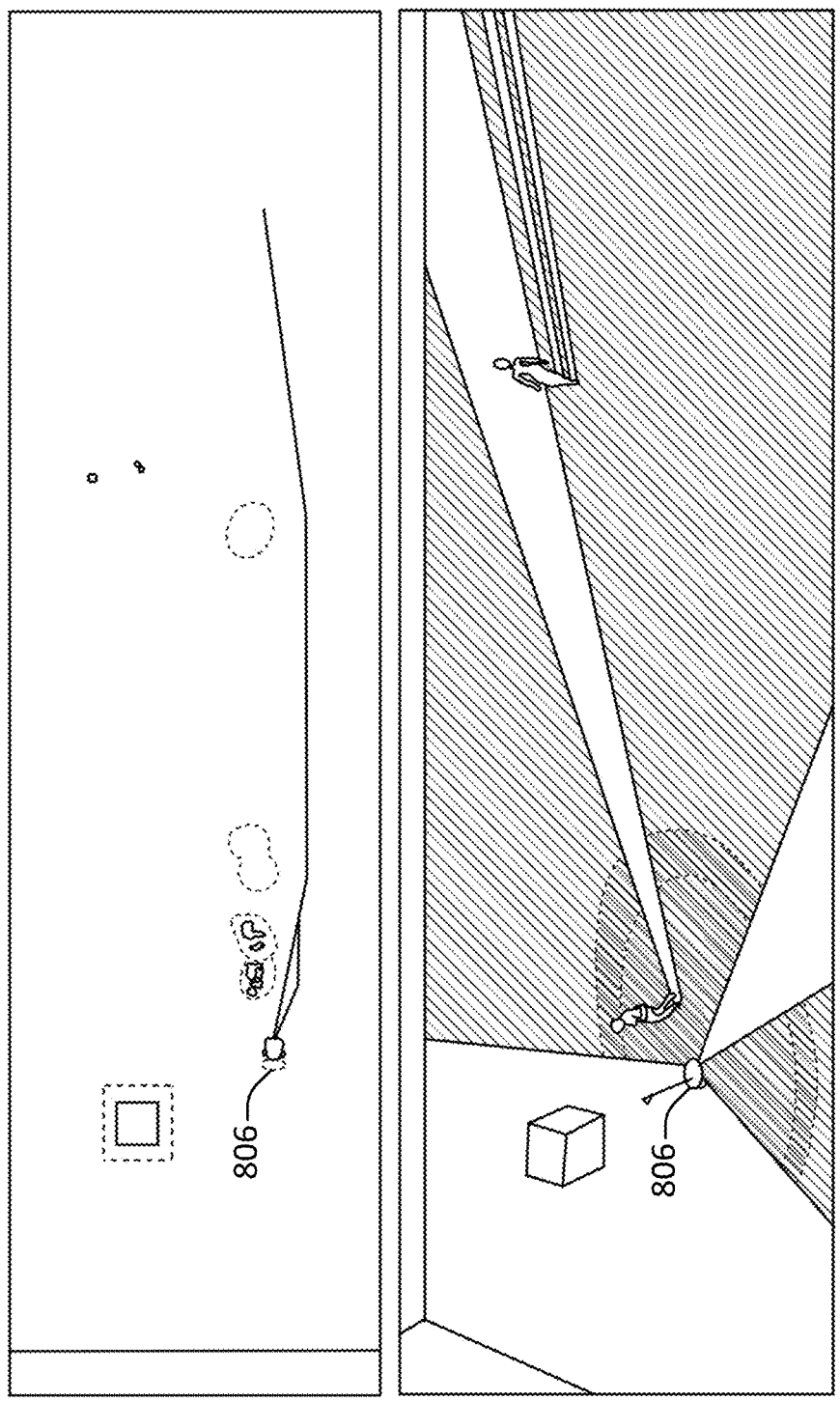

In FIGS. 9 and 10, the robot is shown moving along the updated path and avoiding the human. In this way, the robot can socially accommodate the human instead of requiring that the human change course to accommodate the robot. In FIG. 11, the robot is shown on a reverse course. Due to the location and predicted path of the humans in the room, the reverse path to the original location is different than the original path.

Figure 12:
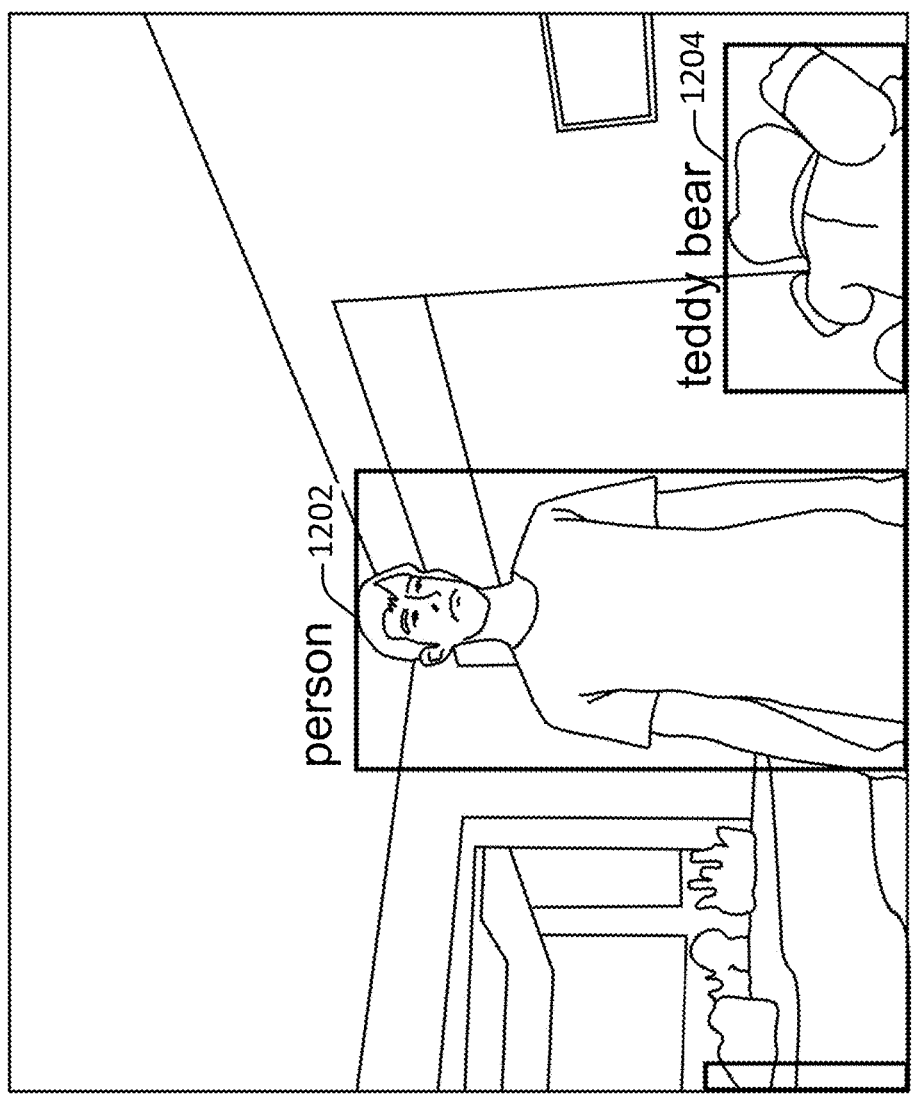
FIG. 12, FIG. 13, and FIG. 14 illustrate images generated in accordance with one or more embodiments.
Figure 13:
Figure 14:
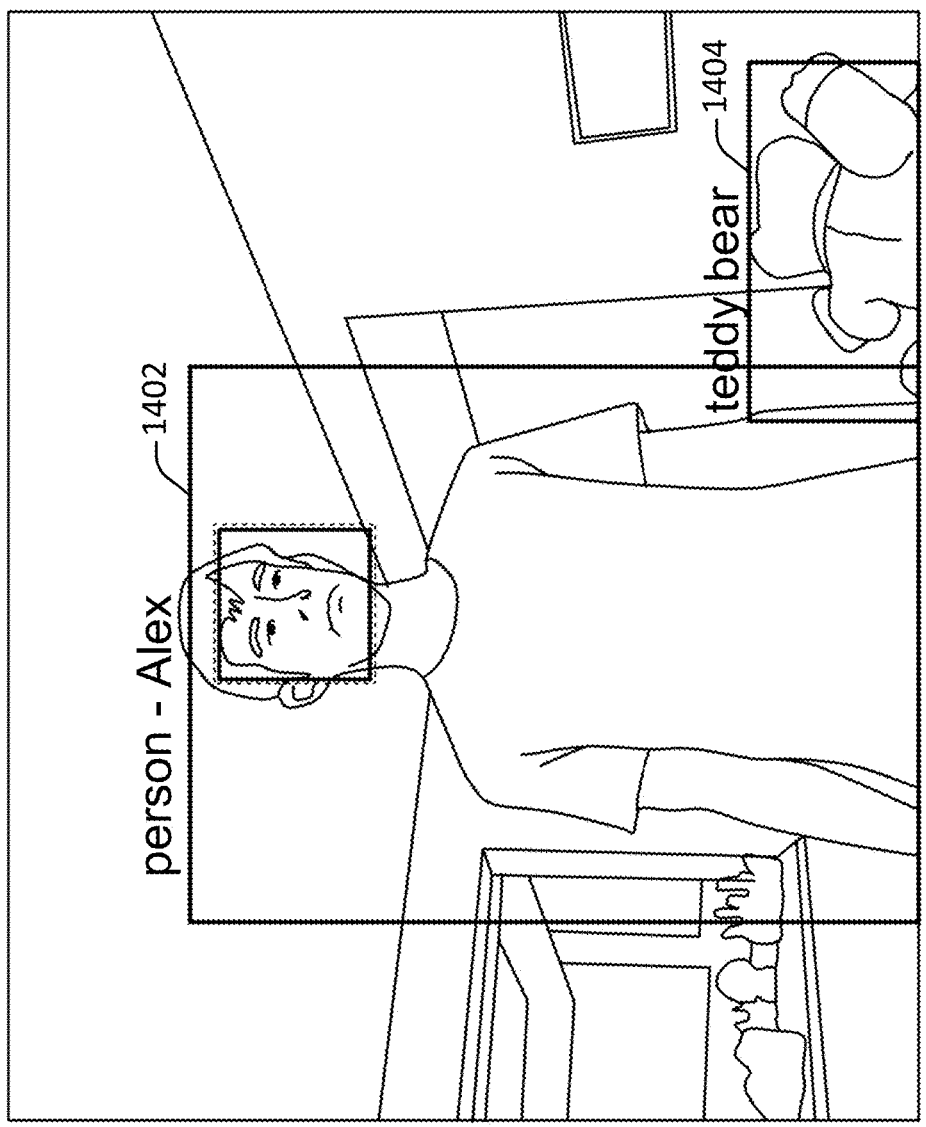

FIGS. 12 through 14 illustrate images generated in accordance with one or more embodiments. FIG. 12 shows an input image 1202 received from a camera at the robot. The robot performs object recognition on the image 1202 to determine a bounding box 1202 for an object and to identify the object within the bounding box 1202 as a person. Similarly, the robot performs object recognition on the image 1202 to determine a bounding box 1204 for an object and to identify the object within the bounding box 1204 as a teddy bear.

Object identification may be performed in association with depth data captured from a depth sensor at the robot. For example, FIG. 13 illustrates a depth map 1300 associated with the image 1200. In the depth map 1300, both a person and a chair are identified.

Additional data may be identified over time. For example, successive images or video data may be captured as the robot and/or person move through space. The collection of additional data may allow for refinements on the object identification. For instance, in the additional input image 1400 shown in FIG. 14, the person within the bounding box 1202 is identified by name as Alex. Such identification may be performed based on accessing a directory of photos, based on past interactions with the person, based on a name tag, and/or based on any other suitable mechanism for identification.

Figure 15:
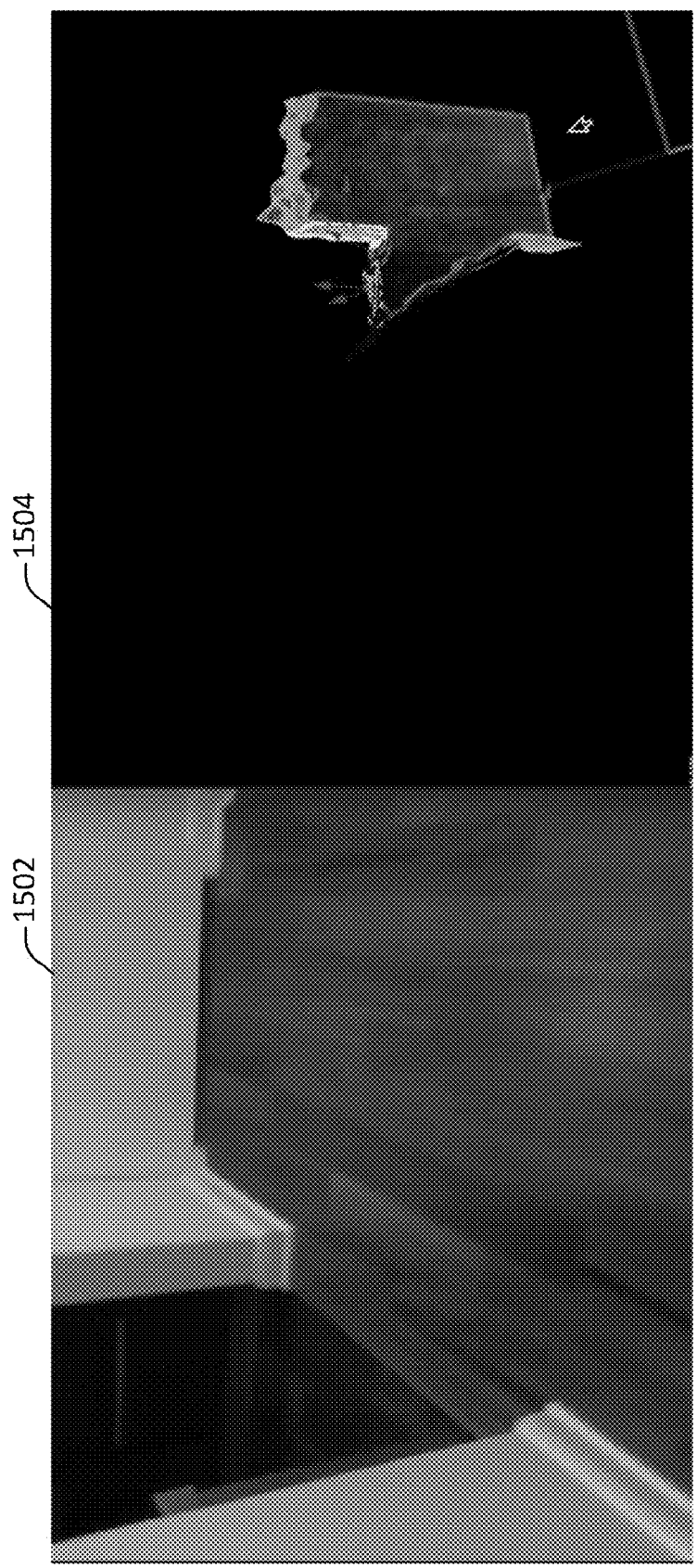
FIGS. 15 and 16 illustrate images generated in accordance with one or more embodiments.
Figure 16:

FIGS. 15 and 16 illustrate images generated in accordance with one or more embodiments. FIG. 15 shows an image pane 1502 depicting image data captured from a camera mounted on the robot. FIG. 15 also shows an image pane 1504 depicting the construction of a three-dimensional model based in part on the image data depicted in 1502. In the image pane 1504, surfaces in a virtual three-dimensional environment are constructed that correspond with the surfaces depicted in the image 1502. The construction of surfaces in the virtual three-dimensional environment may be performed based on the collection of multiple images from different perspectives. Alternatively, or additionally, depth information collected from one or more depth sensors may be employed.

According to various embodiments, as more information is collected, a more comprehensive three-dimensional model may be constructed. For example, FIG. 16 shows a three-dimensional model 1600 of an environment determined based on sensor data received by the robot. Such a model may be determined based on one or more of the visual data, data collected from one or more depth sensors, data collected from one or more other sensors, or a combination thereof.

In some implementations, the model may be coded by color or other metadata. For instance, the three-dimensional model 1600 is coded such that horizontal surfaces such as the floor appear in purple, while vertical surfaces such a wall appear in green.

Figure 5:
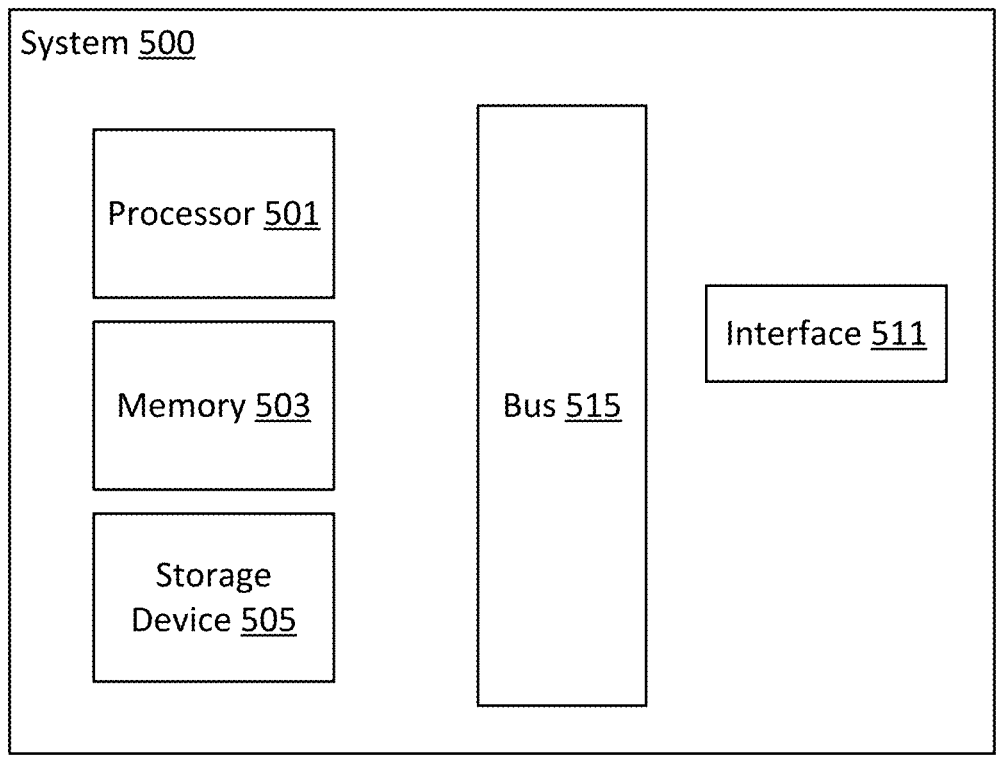
FIG. 5 illustrates one example of a computing device.

FIG. 5 illustrates one example of a computing device. According to various embodiments, a system 500 suitable for implementing embodiments described herein includes a processor 501, a memory module 503, a storage device 505, an interface 511, and a bus 515 (e.g., a PCI bus or other interconnection fabric.) System 500 may operate as variety of devices such as robot, remote server, or any other device or service described herein. Although a particular configuration is described, a variety of alternative configurations are possible. The processor 501 may perform operations such as those described herein. Instructions for performing such operations may be embodied in the memory 503, on one or more non-transitory computer readable media, or on some other storage device. Various specially configured devices can also be used in place of or in addition to the processor 501. The interface 511 may be configured to send and receive data packets over a network. Examples of supported interfaces include, but are not limited to: Ethernet, fast Ethernet, Gigabit Ethernet, frame relay, cable, digital subscriber line (DSL), token ring, Asynchronous Transfer Mode (ATM), High-Speed Serial Interface (HSSI), and Fiber Distributed Data Interface (FDDI). These interfaces may include ports appropriate for communication with the appropriate media. They may also include an independent processor and/or volatile RAM. A computer system or computing device may include or communicate with a monitor, printer, or other suitable display for providing any of the results mentioned herein to a user.

Any of the disclosed implementations may be embodied in various types of hardware, software, firmware, computer readable media, and combinations thereof. For example, some techniques disclosed herein may be implemented, at least in part, by non-transitory computer-readable media that include program instructions, state information, etc., for configuring a computing system to perform various services and operations described herein. Examples of program instructions include both machine code, such as produced by a compiler, and higher-level code that may be executed via an interpreter. Instructions may be embodied in any suitable language such as, for example, Java, Python, C++, C, HTML, any other markup language, JavaScript, ActiveX, VBScript, or Perl. Examples of non-transitory computer-readable media include, but are not limited to: magnetic media such as hard disks and magnetic tape; optical media such as flash memory, compact disk (CD) or digital versatile disk (DVD); magneto-optical media; and other hardware devices such as read-only memory ("ROM") devices and random-access memory ("RAM") devices. A non-transitory computer-readable medium may be any combination of such storage devices.

In the foregoing specification, various techniques and mechanisms may have been described in singular form for clarity. However, it should be noted that some embodiments include multiple iterations of a technique or multiple instantiations of a mechanism unless otherwise noted. For example, a system uses a processor in a variety of contexts but can use multiple processors while remaining within the scope of the present disclosure unless otherwise noted. Similarly, various techniques and mechanisms may have been described as including a connection between two entities. However, a connection does not necessarily mean a direct, unimpeded connection, as a variety of other entities (e.g., bridges, controllers, gateways, etc.) may reside between the two entities.

In the foregoing specification, reference was made in detail to specific embodiments including one or more of the best modes contemplated by the inventors. While various implementations have been described herein, it should be understood that they have been presented by way of example only, and not limitation. For example, some techniques and mechanisms are described herein in the context of cleaning tasks. However, the techniques of the present invention apply to a wide variety of tasks. Particular embodiments may be implemented without some or all of the specific details described herein. In other instances, well known process operations have not been described in detail in order not to unnecessarily obscure the present invention. Accordingly, the breadth and scope of the present application should not be limited by any of the implementations described herein, but should be defined only in accordance with the claims and their equivalents.

The invention claimed is:

1. A method implemented at a robot, the method comprising:

autonomously traversing a physical environment along a first path from a first location to a second location via a mobility apparatus, the first path determined based on sensor data collected from a sensor module at the robot, the sensor data characterizing the physical environment;

autonomously identifying via a processor a human located within the physical environment;

identifying a role associated with the human;

determining a communication mode for communicating with the human based on the identified role;

autonomously determining via the processor a second path through the physical environment, the human being predicted to traverse the second path in the future based on the identified role;

autonomously determining a first one or more future predicted distances between the human and the robot were the robot to follow the first path and were the human to follow the second path;

autonomously determining via the processor that a first predicted distance of the first one or more future predicted distances falls below a designated threshold;

autonomously determining via the processor a third path through the physical environment, the third path ending at the second location, the third path being determined based on the second path so that a second one or more future predicted distances between the human and the robot were the robot to follow the first path and were the human to follow the second path each exceed the designated threshold;

autonomously updating the traversal of the physical environment from the first path to the third path; and presenting a visual cue indicating a navigational goal for the robot based on the third path and the communication mode.

2. The method recited in claim 1, the method further comprising:

determining a model of the physical environment based on the sensor data, the model representing one or more surfaces within the physical environment.

3. The method recited in claim 2, wherein the model is a three-dimensional model, the three-dimensional model representing one or more stationary physical objects, the first and third paths being determined to avoid the one or more stationary physical objects.

4. The method recited in claim 1, wherein predicting the second path comprises identifying a first plurality of locations, each of the first plurality of locations being associated with a first respective point in time, the human being present at each of the first plurality of locations at the first respective point in time.

5. The method recited in claim 4, wherein predicting the second path further comprises determining a second predicted plurality of locations, each of the second predicted plurality of locations being associated with a second respective point in time, the human being predicted to be present at each of the second plurality of locations at the second respective point in time.

6. The method recited in claim 1, wherein the robot includes a communication interface facilitating autonomous communication with the human.

7. The method recited in claim 1, wherein the sensor module includes a camera, and wherein the sensor data includes image data, and wherein the human is identified at least in part by analyzing the image data via the processor.

8. The method recited in claim 1, wherein the sensor module includes a depth sensor, and wherein the sensor data includes depth information, and wherein predicting the second path involves analyzing the depth information.

9. A robot comprising:

a sensor module configured to collect sensor data characterizing a physical environment;

a mobility apparatus configured to traverse the physical environment; and a processor configured to:
determine a first path from a first location in the physical environment to a second location in the physical environment;

instruct the mobility apparatus to traverse the physical environment along the first path;

identify a human located within the physical environment;

identify a role associated with the human;

determine a communication mode for communicating with the human based on the identified role;

determine a second path through the physical environment, the human being predicted to traverse the second path in the future based on the identified role;

determine a first one or more future predicted distances between the human and the robot were the robot to follow the first path and were the human to follow the second path;

determine that a first predicted distance of the first one or more future predicted distances falls below a designated threshold;

determine via the processor a third path through the physical environment, the third path ending at the second location, the third path being determined based on the second path so that a second one or more future predicted distances between the human and the robot were the robot to follow the first path and were the human to follow the second path each exceed the designated threshold;

instruct the mobility apparatus to update the traversal of the physical environment from the first path to the third path; and present a visual cue indicating a navigational goal for the robot based on the third path and the communication mode.

10. The robot recited in claim 9, wherein the processor is further operable to:

determine a three-dimensional model of the physical environment based on the sensor data, the three-dimensional model representing one or more surfaces within the physical environment, the three-dimensional model further representing one or more stationary physical objects, the first and third paths being determined to avoid the one or more stationary physical objects.

11. The robot recited in claim 9, wherein predicting the second path comprises identifying a first plurality of locations, each of the first plurality of locations being associated with a first respective point in time, the human being present at each of the first plurality of locations at the first respective point in time, and wherein predicting the second path further comprises determining a second predicted plurality of locations, each of the second predicted plurality of locations being associated with a second respective point in time, the human being predicted to be present at each of the second plurality of locations at the second respective point in time.

12. One or more non-transitory machine readable media having instructions stored thereon for performing a method, the method comprising:

autonomously traversing a physical environment along a first path from a first location to a second location via a mobility apparatus, the first path determined based on sensor data collected from a sensor module at the robot, the sensor data characterizing the physical environment;

autonomously identifying via a processor a human located within the physical environment;

identifying a role associated with the human;

determining a communication mode for communicating with the human based on the identified role;

autonomously determining via the processor a second path through the physical environment, the human being predicted to traverse the second path in the future based on the identified role;

autonomously determining a first one or more future predicted distances between the human and the robot were the robot to follow the first path and were the human to follow the second path;

autonomously determining via the processor that a first predicted distance of the first one or more future predicted distances falls below a designated threshold;

autonomously determining via the processor a third path through the physical environment, the third path ending at the second location, the third path being determined based on the second path so that a second one or more future predicted distances between the human and the robot were the robot to follow the first path and were the human to follow the second path each exceed the designated threshold;

autonomously updating the traversal of the physical environment from the first path to the third path; and presenting a visual cue indicating a navigational goal for the robot based on the third path and the communication mode.

* * * * *